(12) United States Patent
Hashimoto

(10) Patent No.: US 7,672,435 B2
(45) Date of Patent: Mar. 2, 2010

(54) RADIATION THERAPY APPARATUS

(75) Inventor: Teruo Hashimoto, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 12/035,143

(22) Filed: Feb. 21, 2008

(65) Prior Publication Data
US 2008/0205599 A1 Aug. 28, 2008

(30) Foreign Application Priority Data
Feb. 23, 2007 (JP) ............................. 2007-044165

(51) Int. Cl.
*G21K 1/02* (2006.01)
*A61N 5/10* (2006.01)

(52) U.S. Cl. ........................................ 378/148; 378/65

(58) Field of Classification Search ................... 378/65, 378/145–153
See application file for complete search history.

(56) References Cited

U.S. PATENT DOCUMENTS

| | | | |
|---|---|---|---|
| 4,868,844 A * | 9/1989 | Nunan | 378/152 |
| 5,067,144 A | 11/1991 | Aitkenhead et al. | |
| 2002/0126799 A1 | 9/2002 | Saladin et al. | |
| 2005/0047856 A1 * | 3/2005 | Allswede | 403/326 |
| 2006/0067480 A1 * | 3/2006 | Juschka et al. | 378/150 |
| 2007/0176126 A1 | 8/2007 | Hashimoto | |

FOREIGN PATENT DOCUMENTS

| | | |
|---|---|---|
| DE | 970 771 | 12/1958 |
| DE | 195 36 804 A1 | 4/1997 |
| EP | 1 712 254 A1 | 10/2006 |
| GB | 450 874 | 7/1936 |
| JP | 2543373 | 7/1996 |
| JP | 2002-253686 | 9/2002 |
| JP | 2003-210594 | 7/2003 |
| JP | 2007-37828 | 2/2007 |

* cited by examiner

*Primary Examiner*—Irakli Kiknadze
(74) *Attorney, Agent, or Firm*—Oblon, Spivak, McClelland, Maier & Neustadt, L.L.P.

(57) ABSTRACT

A radiation therapy apparatus has a multi-leaf collimator device, a driving gear, a torque wire and a driving unit. The multi-leaf collimator device has a pair of collimator components which respectively comprise a plurality of leaves arranged close to one another such that the leaves face one another across an irradiation axis, and configured to set a desired irradiation field by individually moving the leaves. The driving gear is engaged with a gear tooth of the each leaf, respectively. The torque wire is connected to a shaft center of the driving gear, respectively. The driving unit is configured to drive the driving gears through the torque wire.

10 Claims, 14 Drawing Sheets

RADIATION THERAPY APPARATUS

BACKGROUND OF THE INVENTION

1. Field of the Invention

The present invention relates to a radiation therapy apparatus used for a therapy of diseases such as malignant tumors, and particularly to the radiation therapy apparatus including a multi-leaf collimator device which allows an extent of an object that is exposed to radiation (which will be referred to as an "irradiation field" hereafter) to be set with high precision.

2. Description of the Related Art

From the perspective of radiation protection, the radiation therapy apparatus includes a collimator device formed of a material the nature of which renders it impermeable to radiation such as tungsten or the like, thereby allowing the exposure to radiation to be limited to a therapy part including a body. Such a collimator device needs to have a function of carefully forming the irradiation field that approximates a shape of the therapy part without a formation of a penumbra. Accordingly, such a collimator device has a first collimator and a second collimator arranged in the irradiation direction such that they overlap.

With such an arrangement, the first collimator provided on a near side of a radiation source is configured in a form of a single unit comprising a pair of members disposed such that they face each other across an irradiation axis. Such an arrangement allows that the members drive so as to adjust a distance therebetween. For example, the members drive along an arc-shaped path around the radiation source as a center. On the other hand, the second collimator provided on a far side of the radiation source is configured in the form of a pair of collimator components (blocks) such that the collimator components face each other across the irradiation axis in an orthogonal direction to a moving direction of the first collimator. Each of the collimator components of the second collimator has multiple leaves arranged close to one another, which can be individually moved so as to adjust a distance therebetween along the arc-shaped path around the radiation source as the center.

The second collimator is called "multi-leaf collimator", which includes, for example, a block pair composed of several ten leaves that are closely gathered side by side. The leaves of the second collimator each have the arc-shaped path and are individually driven movably along the arc-shaped path with a driving device provided to each leaf. Thus, the radiation field of an irregular shape can be formed by combining an operation of moving the first collimator composed of a pair of opposing separate members to get close to/away from each other in an X direction and an operation of individually moving the leaves of the second collimator, which are gathered opposite to each other, so as to get close to/away from each other in a Y direction. Here, the first collimator and the second collimator may be collectively referred to as "multi-leaf collimator".

FIG. 15 schematically is one leaf 41 of the second collimator and a driving device 43 for driving the leaf. Referring to FIG. 15, how to drive the leaf 41 and control its position is described below in brief.

The leaf 41 of FIG. 15 is formed in a fan shape that converges to a radiation source as seen in a plan view and in a plate-like or wedge shape as seen in a side view. Further, an outer edge 41a of the leaf 41 is curved along the arc-shaped path around the radiation source as the center. A gear tooth is cut in the arc-shaped path plane, that is, the curved outer edge 41a. A driving gear 43a is engaged with the tooth of the outer edge 41a.

The driving gear 43a is fixed to a tip end of a shaft 43b. The shaft 43b is driven based on a driving force transmitted from a motor 43c as a driving source through a driving force transmitting mechanism such as a worm gear 43d. A potentiometer 43e and an encoder 43f are arranged to detect a torque, and function as a position detecting device for the leaf 41. The motor 43c is controlled by an additional control device based on information from the potentiometer 43e and the encoder 43f, and the leaf 41 is set in a desired position to form a predetermined radiation field (see "Japanese Patent Publication (Laid-open: KOKAI) No. 2002-253686", for example).

In the case of detecting penumbra, leaves of the multi-leaf collimator can be moved closer to/away from each other in a horizontal direction without requiring a complicated structure such as moves the leaves concentrically along the arc-shaped path around the radiation source as the center. One known technique applicable to this case is to drive a threaded shaft connected to each leaf with a motor through a flexible cable (see "Japanese Patent No. 2543373", for example).

As described above, the technique disclosed in "Japanese Patent Publication No. 2002-253686" requires a mechanism for transmitting a torque of a motor to each of leaves of the second collimator through various gears and a shaft in order to individually move the leaves. Such a driving force transmitting mechanism needs to be provided to each leaf. From the viewpoint of radioprotection, in recent years, there is an increasing demand to further match a radiation field to an irregular shape of a treated area. To meet the demand, it has been examined whether to increase the number of leaves.

However, if the number of leaves is increased, it is necessary to prepare as many driving force transmitting mechanisms such as the motor, the gear and the shaft, as the number of leaves. This causes a problem about how to secure an area enough to arrange as many driving force transmitting mechanisms as the number of leaves in a limited space. Thus, increasing the number of leaves leads to a problem of enlarging the collimator to limit a treatment space of a radiation therapy apparatus itself.

Further, in the above driving force transmitting mechanism, a torque of the motor is transmitted to each leaf through the gear and the shaft, which imposes a limitation that the motor should be placed in a direction parallel or vertical to a moving axis of each leaf. Thus, the degree of freedom of arrangement is low. As a result, it is difficult to increase the number of leaves. Further, accumulative backlash between engaged gears causes an error in a moving amount of leaves and thus, it is necessary to take a measure for eliminating the backlash.

On the other hand, the technique disclosed in "Japanese Patent No. 2543373" transmits a torque of the motor to the threaded shaft connected to each leaf through a flexible cable to move the leaves by pushing or pulling in a horizontal direction. In the case of moving leaves along the arc-shaped path according to this technique, the flexible cable extends or contracts, resulting in a problem that the moving of each leaf cannot be managed with accuracy.

SUMMARY OF THE INVENTION

The present invention has taken into consideration the above-described problems and it is an object of the present invention to provide the radiation therapy apparatus which a torque wire having a high rotation following allows transmission of a torque of the motor as a driving source to a tip end with accuracy while keeping a high flexibility to a bent portion. Accordingly, the torque wire transmits a torque of the motor to a driving gear with accuracy regardless of orientation and angle of the motor, making it possible to move the leaves concentrically along the arc-shaped path about the radiation source to get close to/away from each other.

Further, the motor achieves the very high degree of freedom of arrangement relative to the moving axis of the leaves and is placed in a dead space in the collimator. In short, an internal space of the collimator device is efficiently utilized, and the number of leaves is increased without enlarging the collimator device. As a result, the irradiation field is matched more with a treatment site without reducing the space for the treatment, so as to enable safer radiotherapy for the object. Further, the driving gear of the driving device is a one-stage gear, so backlash is easily adjusted and operation accuracy is improved.

Further, the present invention has taken into consideration the above-described problems and it is an object of the present invention to provide the radiation therapy apparatus which the moving amount of each leaf is easily detected using a torque motor with a built-in encoder, making it to simplify a complicated mechanism using a number of gears, and a potentiometer or an encoder in combination to control the moving amount.

Further, the present invention has taken into consideration the above-described problems and it is an object of the present invention to provide the radiation therapy apparatus which a displacement or position detection error due to an influence of backlash or friction between gears is suppressed. Hence, a leaf position is accurately detected and the irradiation field is accurately matched with an affected area.

To solve the above-described problems, the present invention provides the radiation therapy apparatus, comprising: a multi-leaf collimator device having a pair of collimator components which respectively comprise a plurality of leaves arranged close to one another such that the leaves face one another across an irradiation axis, and configured to set a desired irradiation field by individually moving the leaves; a driving gear engaged with a gear tooth of the each leaf, respectively; a torque wire connected to a shaft center of the driving gear, respectively; and a driving unit configured to drive the driving gears through the torque wire.

DESCRIPTION OF THE PREFERRED EMBODIMENTS

Figure 1:
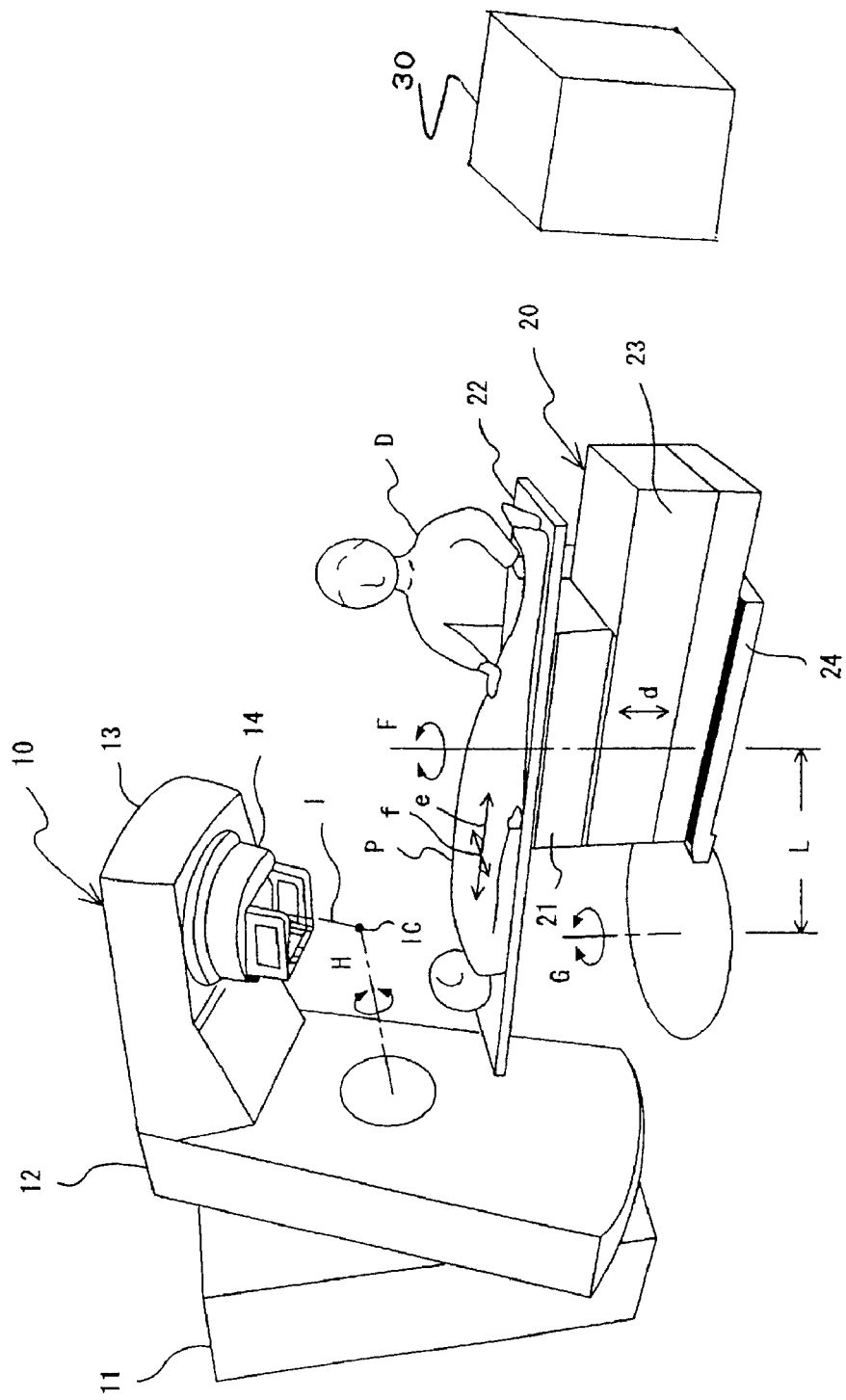
FIG. 1 is an external view which shows a usage condition of the radiation therapy apparatus according to a present embodiment.

Detailed description will be made with reference to FIG. 1 through FIG. 14 regarding a radiation therapy apparatus including a multi-leaf collimator device according to an embodiment of the present invention. It should be noted that, in these drawings, the same components are denoted by the same reference numerals.

FIG. 1 is an external view which shows a usage condition of the radiation therapy apparatus according to a present embodiment. First, description will be made in a schematic fashion with reference to FIG. 1 regarding a configuration of the radiation therapy apparatus according to the present embodiment.

In broad terms, the radiation therapy apparatus has an irradiation device 10 which uses a radiation source to irradiate a predetermined direction, a therapy table 20 on which an object (a person who needs a therapy) P, including a focus, lies and which sets a positioning of a therapy part to be irradiated, and a control device 30 which organically controls a components of the radiation therapy apparatus, e.g., the irradiation device 10 and the therapy table 20.

The irradiation device 10 includes a fixed frame 11 installed on a floor, a turnable frame 12 which is turnably supported by the fixed frame 11, an irradiation head 13 provided to a tip portion extending in the horizontal direction from one end of the turnable frame 12, and a collimator device 14 which is a built-in component of the irradiation head 13. With such an arrangement, the turnable frame 12 can be turned with respect to the fixed frame 11 over approximately 360 degrees around a rotation center axis "H" extending in the horizontal direction. Furthermore, the collimator device 14 is provided such that it can be turned with respect to the irradiation head 13 around an irradiation axis "I". It should be noted that the intersection of a rotation center axis "H" for the turnable frame 12 and the irradiation axis "I" will be referred to as the "isocenter (IC)" hereafter. With such an arrangement, the turnable frame 12 is configured such that it can be turned according to various kinds of irradiation, examples of which include a rotation irradiation, a pendulum irradiation, an intermittent irradiation, etc.

Furthermore, the therapy table 20 is installed on the floor such that it can be turned over a predetermined angle range in a direction of arrow "G" along an arc with the isocenter IC as a center. Furthermore, a table-top 22, on which the object P can lie, is provided to a top of the therapy table 20. Here, the table-top plate 22 is supported by an upper portion mechanism 21. The upper portion mechanism 21 includes a mechanism which allows the table-top 22 to be moved in a longitudinal direction indicated by an arrow "e" and a lateral direction indicated by an arrow "f".

Furthermore, the upper portion mechanism 21 is supported by an elevator mechanism 23. The elevator mechanism 23 has a link mechanism, for example. Such an arrangement allows the elevator mechanism 23 itself to be moved in a vertical direction indicated by an arrow "d", thereby allowing the upper portion mechanism 21 and the table-top 22 to be moved in a predetermined range in the vertical direction. Moreover, the elevator mechanism 23 is supported by a lower portion mechanism 24. The lower portion mechanism includes a mechanism which allows the elevator mechanism 23 to be turned in the direction indicated by an arrow "F", with the position that is distant from the isocenter IC by a distance "L" as the center. Such an arrangement allows the upper portion mechanism 21 and the table-top 22 to be turned in a predetermined range of angle in the direction indicated by the arrow "F", in addition to the elevator mechanism 23.

It should be noted that such an arrangement allows a medical staff "D" such as a surgeon or the like to operate an operation unit provided to the control device 30, thereby setting the positioning of the object P and adjusting the collimator device 14 which defines an irradiation field at a radiation therapy.

It is important for the radiation therapy to irradiate only the therapy part in a concentrated manner without damaging a normal tissue. The collimator device 14 controls a position to be irradiated, which protects the normal tissue from being exposed to radiation. With such an arrangement, the collimator device 14 is provided in the form of a built-in component of the irradiation head 13 such that it can be turned around the irradiation axis "I".

Figure 2:
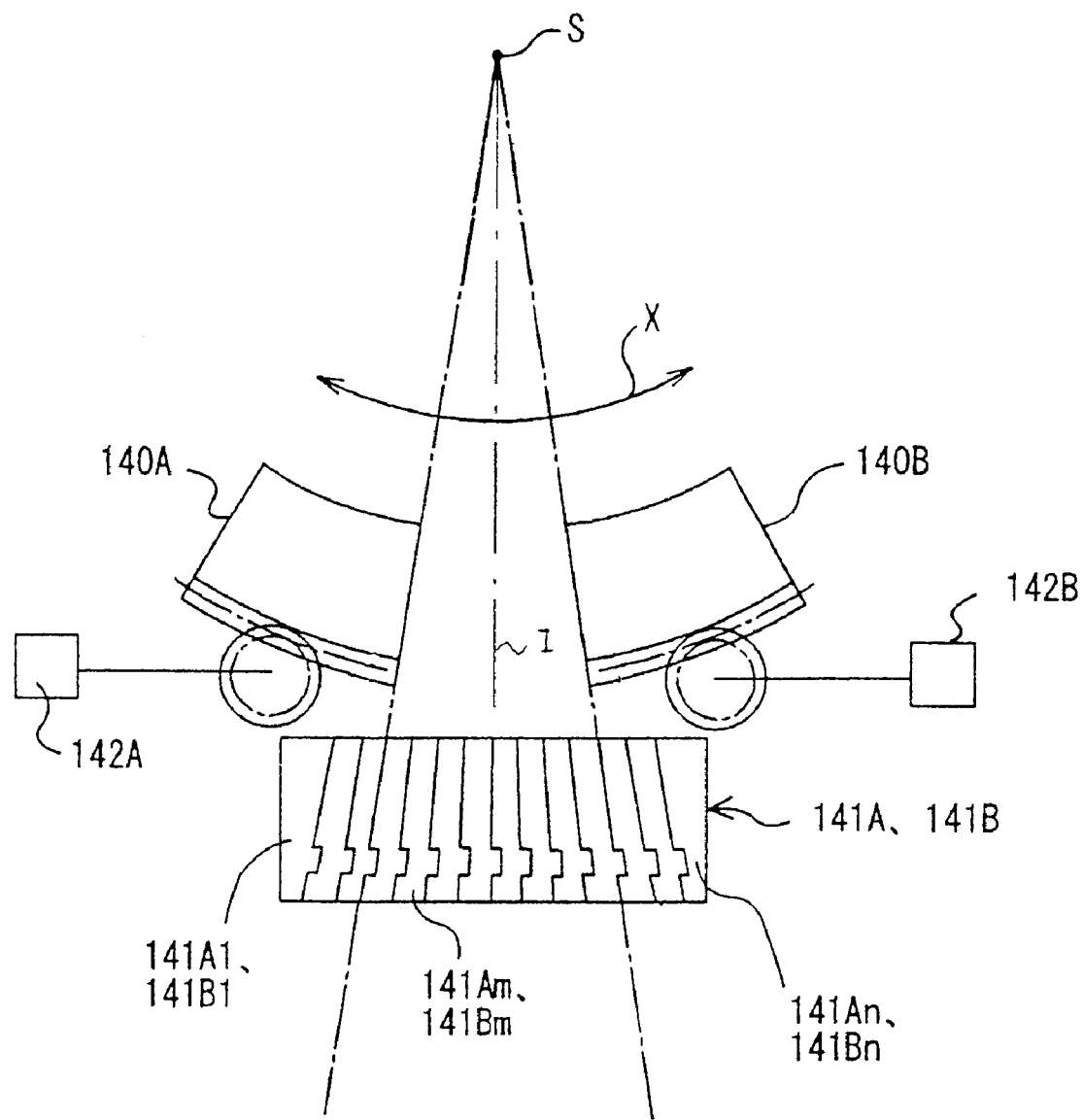
FIG. 2 is a side view, shown a driving direction of the second collimator as a depth direction, which shows the first collimator and the second collimator included the collimator device in the present embodiment.
Figure 3:
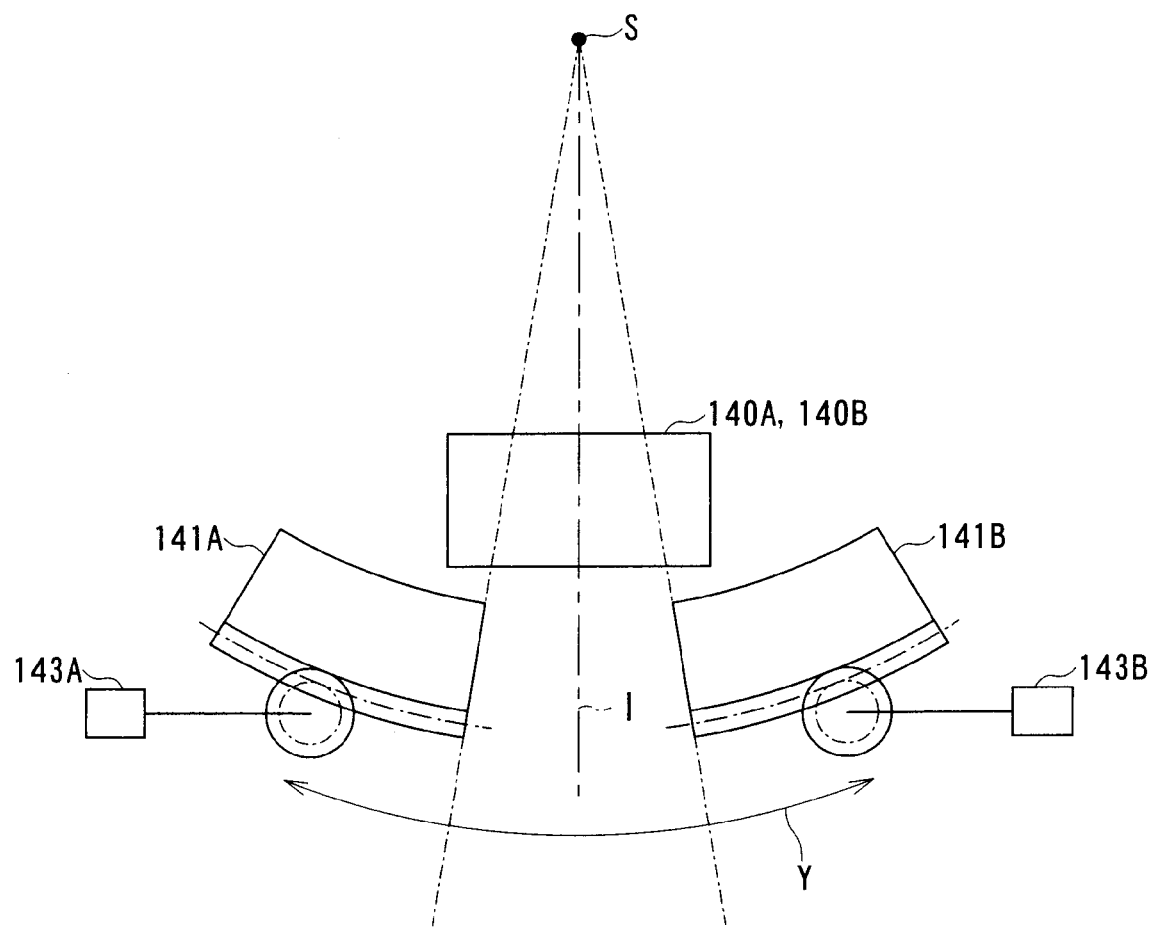
FIG. 3 is a side view, shown a first example of a driving direction of the second collimator as an orthogonal direction, which shows the first collimator and the second collimator provided to the collimator device in the present embodiment.
Figure 4:
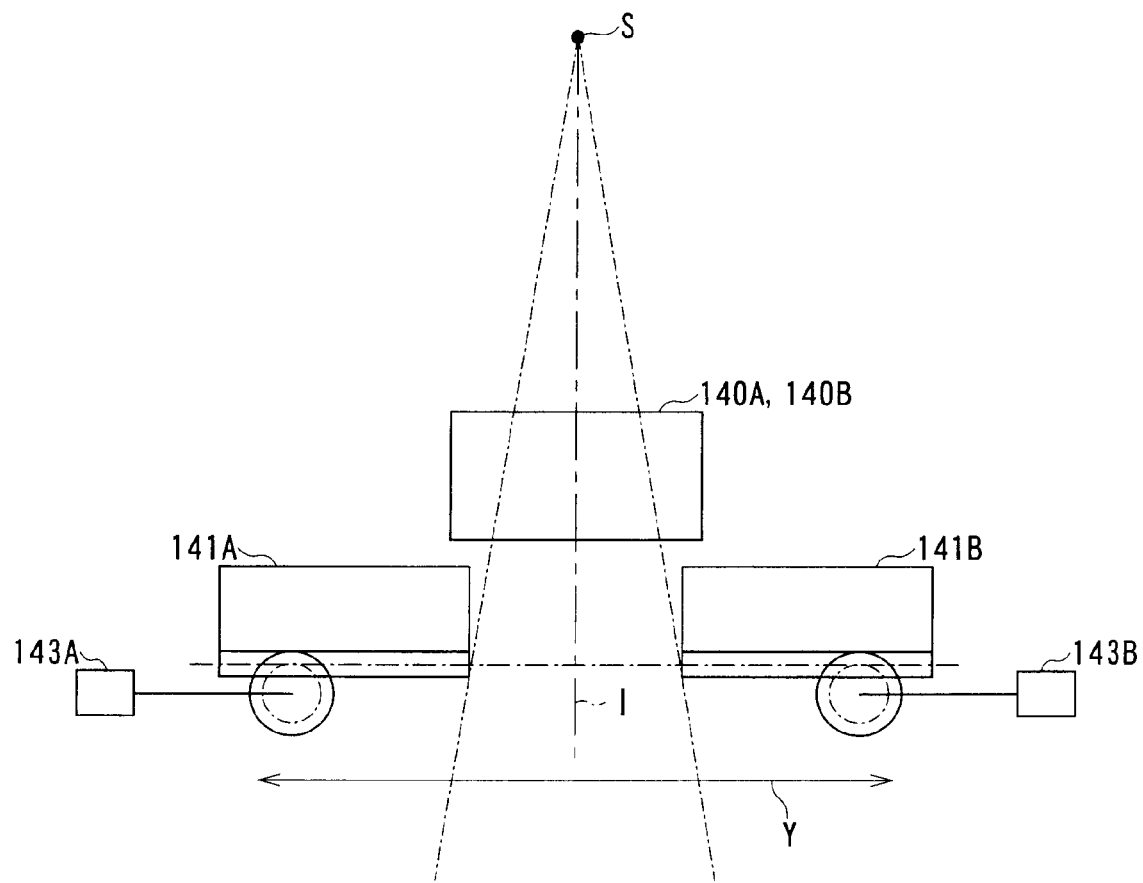
FIG. 4 is a side view, shown a second example of a driving direction of the second collimator as an orthogonal direction, which shows the first collimator and the second collimator provided to the collimator device in the present embodiment.
Figure 5:
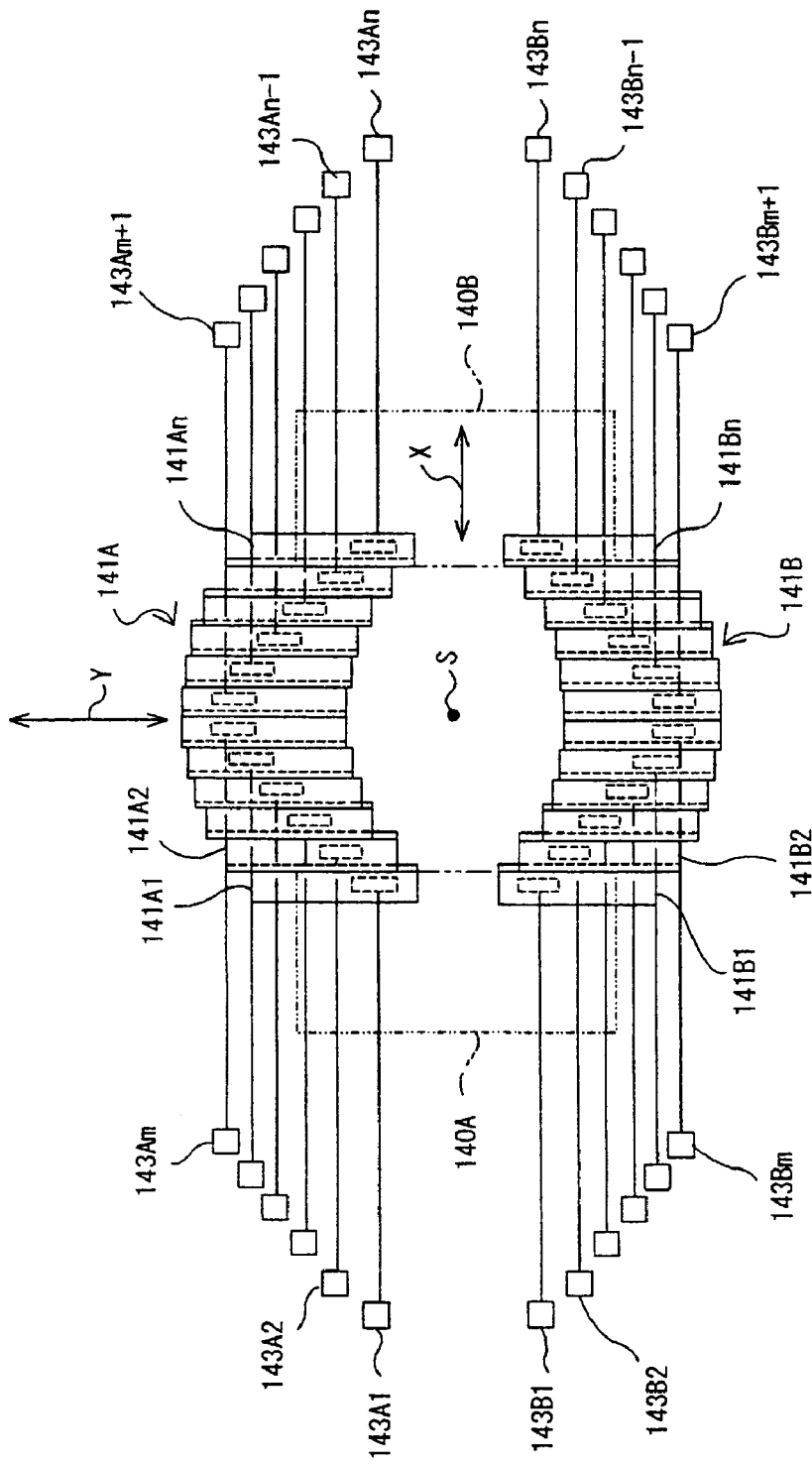
FIG. 5 is a top view which shows a constitution example of the second collimator provided to the collimator device in the present embodiment.
Figure 6:
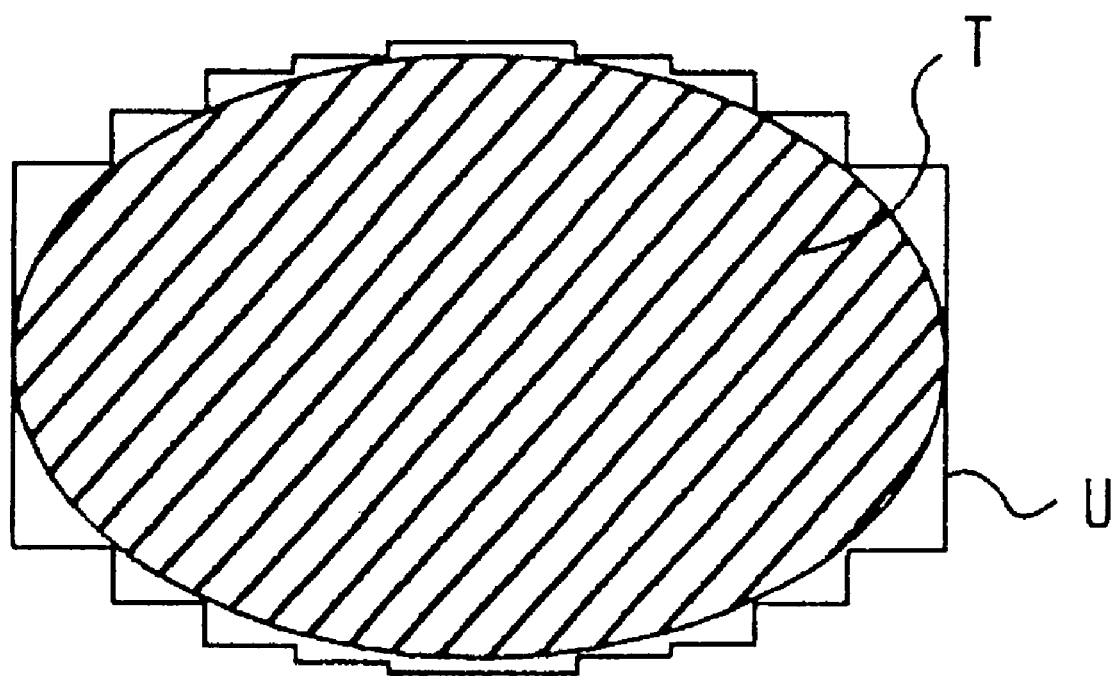
FIG. 6 is a top view which shows the irradiation field example of the second collimator in the present embodiment.

Next, description will be made regarding the collimator device 14 with reference to FIG. 2 through FIG. 7. FIG. 2 is a side view, shown a driving direction of a second collimator 141 as a depth direction, which shows a first collimator 140 and the second collimator 141 included the collimator device 14 in the present embodiment. FIG. 3 is a side view, shown a first example of the driving direction of the second collimator 141 as an orthogonal direction, which shows the first collimator 140 and the second collimator 141 provided to the collimator device 14 in the present embodiment. FIG. 4 is a side view, shown a second example of the driving direction of the second collimator 141 as an orthogonal direction, which shows the first collimator 140 and the second collimator 141 provided to the collimator device in the present embodiment. It should be noted that FIG. 3 and FIG. 4 show the collimator device 14 viewed in an orthogonal direction orthogonal to the direction in which the collimator 14 shown in FIG. 2 is viewed. Furthermore, a housing of the collimator device 14 is not shown in these drawings. FIG. 5 is a top view which shows a constitution example of the second collimator provided to the collimator device 14 in the present embodiment.

As shown in FIG. 2 through FIG. 4, in general, the collimator device 14 has two kinds of collimators (a first collimator 140 and a second collimator 141) formed of a heavy metal such as tungsten or the like. These two kinds of collimators are arranged along the irradiation direction from the radiation source "S" such that they overlap. With such an arrangement, each of the collimators 140 and 141 has a pair of separate components arranged such that they face each other (see the components denoted by reference numerals 140A, 140B, 141A, and 141B in FIG. 2 and FIG. 3). Here, such a pair of components forming the collimator 140 or 141 is differentiated by reference symbols "A" and "B" for convenience of understanding.

With such an arrangement, each of the first collimator component 140A and the second collimator component 140B provided on a near side of the radiation source "S" is configured in the form of a single unit, as clearly shown in FIG. 2. Furthermore, the collimator components 140A and 140B are arranged such that an end face of the collimator component 140A and an end face of the collimator component 140B face each other across the irradiation axis "I". Such an arrangement allows the collimator elements 140A and 140B to be moved in a direction of an arrow "X" along an arc-shaped path around the radiation source "S" as a center by driving devices 142A and 142B, thereby adjusting a distance between the collimator components 140A and 140B.

Also, the second collimator components 141A and 141B provided on a far side of the radiation source "S" can be moved along the arc-shaped path, as clearly shown in FIG. 3. Furthermore, the collimator components 141A and 141B are arranged such that an end face of the collimator component 141A and an end face of the collimator component 141B face each other across the irradiation axis "I". Such an arrangement allows the collimator elements 141A and 141B to be moved by driving devices 143A and 143B in the orthogonal direction to the aforementioned arranging direction of the collimator elements 140A and 140B, i.e., in a direction of an arrow "Y" along the arc-shaped path around the radiation source "S" as the center, thereby adjusting a distance between the collimator components 141A and 141B.

In another example shown in FIG. 4, the second collimator components 141A and 141B are arranged such that the end face of the collimator component 141A and the end face of the collimator component 141B face each other across the irradiation axis "I". Such an arrangement allows the collimator elements 141A and 141B to be moved by the driving devices 143A and 143B in the orthogonal direction to an arranging direction of the first collimator elements 140A and 140B, i.e., in the direction of the arrow "Y" along a straight path, thereby adjusting the distance between the collimator components 141A and 141B.

Note that description will be made below regarding an arrangement which allows the first collimator 140 to be driven in the driving direction "X" as described with reference to FIG. 2, and which allows the second collimator 141 to be driven in the driving direction "Y" as described with reference to FIG. 3.

As shown in FIG. 2, the second collimator component 141A (141B) has multiple leaves 141A1-141An (141B1-141Bn) arranged close to one another. FIG. 5 shows the detailed configuration thereof.

That is to say, driving devices 143A1-143An (143B1-143Bn) are provided to the respective leaves 141A1-141An (141B1-141Bn) forming the second collimator component 141A (141B). Such an arrangement allows the leaves 141A1-141n (141B1-141Bn) to be driven individually in the direction of the arrow "Y" along the arc-shaped path around the radiation source "S" as the center, thereby adjusting the distances therebetween.

Such an arrangement allows the leaves 141A1-141An of the second collimator component 141A and the leaves 141B1-141Bn of the second collimator component 141B to be moved individually in the "Y" direction so as to adjust the distance therebetween, in addition to allowing the first collimator components 140A and 140B to be moved in the "X" direction so as to adjust the distance therebetween. The combination of these operations allows the irradiation field "U", shown in FIG. 6, to be formed in a desired shape such that it approximates the shape of the therapy part "T" which is approximately equal to the focus.

Figure 7:
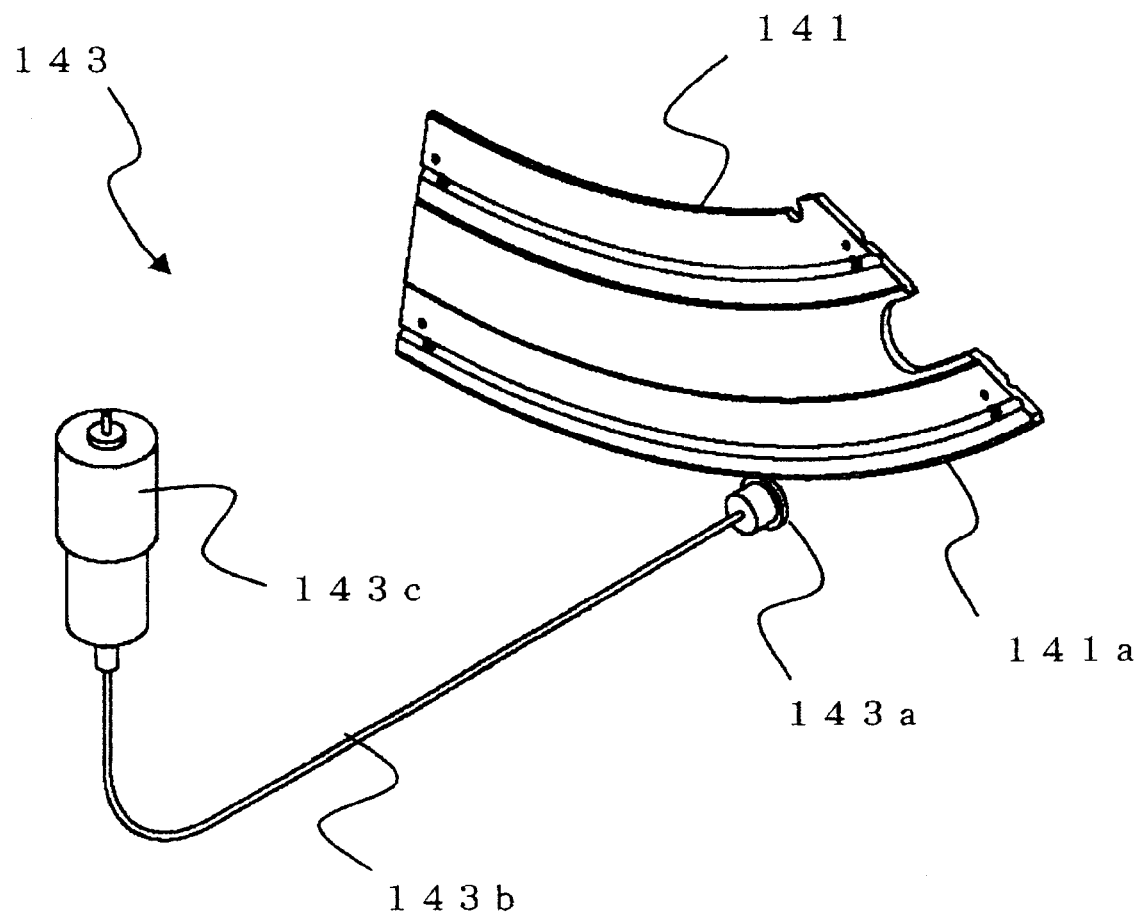
FIG. 7 is a top view which shows an arrangement example and a formation of the irradiation field by arranging the leaves included the second collimator in the present embodiment.

FIG. 7 shows an example of the driving device 143 such as the driving devices 143A1-143An and 143lB1-143Bn for driving the leaf 141 such as the leaves 141A1-141An and 141B1-141Bn.

In the radiation therapy apparatus of this embodiment, the leaves 141A1-141An and 141B1-141Bn of the second collimator components 141A and 141B (hereinafter simply referred to as "leaf 141") are similar to conventional ones. The leaves are formed in a fan shape that converges to the radiation source as seen in a plan view and in a plate-like or wedge shape as seen in a side view. Further, an outer edge of each leaf 141 is curved along the arc-shaped path around the radiation source "S" as the center. A gear tooth 141a is cut in the arc-shaped path plane, that is, the curved outer edge. A driving gear 143a of each of the driving devices 143A1-143An and 143lB1-143Bn (hereinafter simply referred to as "driving device 143") is engaged with the tooth 141a of the outer edge.

The driving device 143 is composed of the driving gear 143a, a torque wire 143b, and a torque motor 143c. That is, the driving device is structured such that one end of the torque wire 143b is connected to the rotation center of the driving gear 143a engaged with the tooth 141a of the outer edge of the leaf 141, and the other end of the torque wire 143b is connected to the torque motor 143c. Thus, a torque of the torque motor 143c is transmitted to the driving gear 143a through the torque wire 143b to drive the leaf 141.

Figure 8:
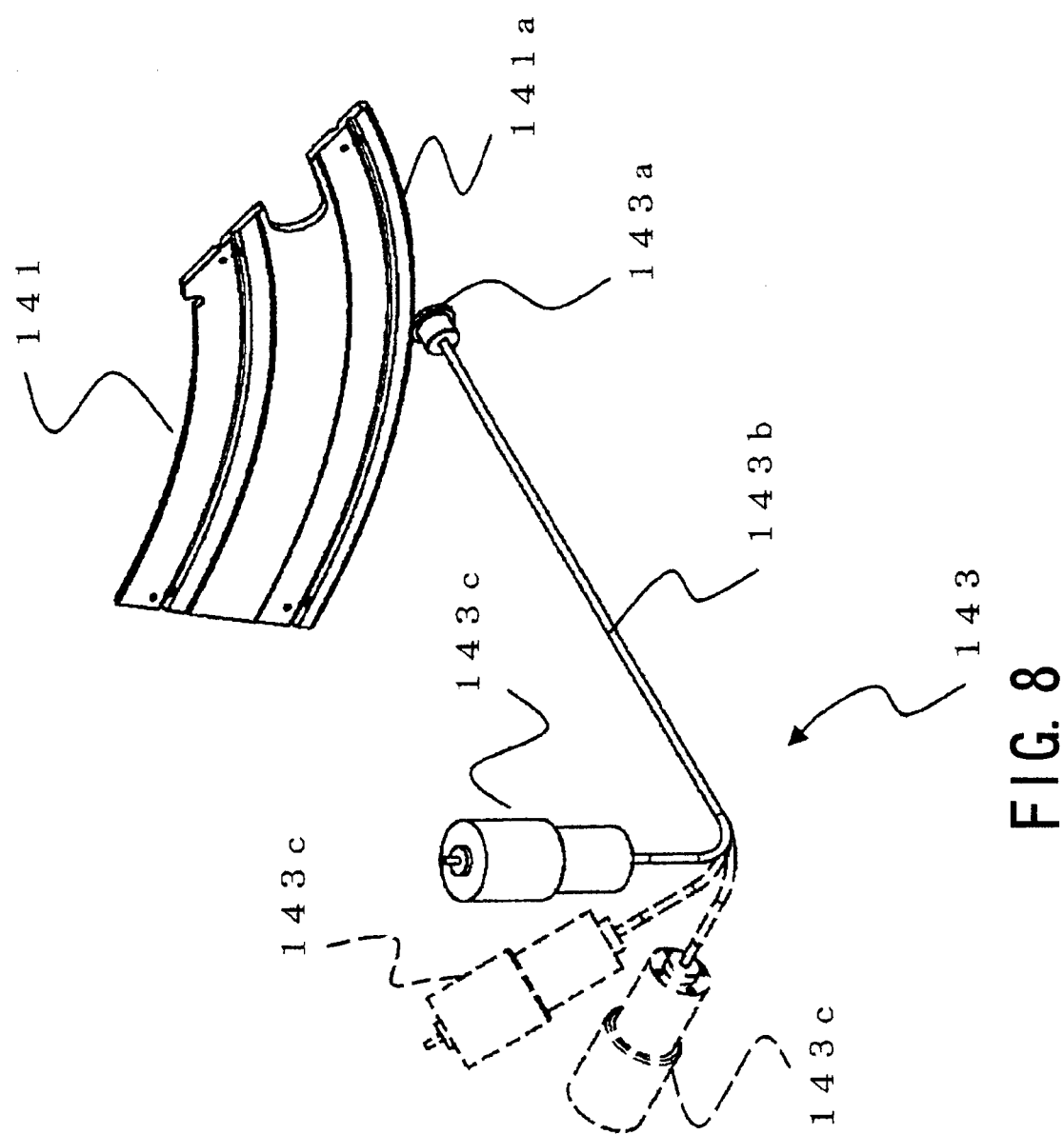
FIG. 8 schematically is an arrangement example of the driving device.

A feature of the torque wire 143b is as follows. That is, the wire has a high rotation following capability and thus, can transmit a torque of a driving force such as a motor to a tip end with accuracy. In addition, the wire has flexibility and thus can keep its high performance even at a bent portion. Hence, as shown in FIG. 8, for example, the torque wire 143b can transmit a torque of the torque motor 143c to the driving gear 143a with accuracy irrespective of orientation and angle of the torque motor 143c, and can move each leaf 141 by a desired amount. In other words, the leaf 141 of the second collimator components 141A and 141B can be moved concentrically about the radiation source along the arc-shaped path to get close to/away from each other. Here, the three torque motors 143c illustrated in FIG. 8 means that one torque motor 143c is arranged in different directions and at different angles by use of the torque wire 143b, not that the number of motors is three.

Thus, the motor 143 achieves the very high degree of freedom of arrangement relative to the moving axis of each leaf 141 and thus can be placed even in a dead space of a container of the collimator 14. In short, an internal space of the collimator can be efficiently utilized, and the number of leaves can be increased without enlarging the collimator 14. As a result, an irradiation field can be more matched with a treatment site without reducing a space for the therapy. This enables safer radiotherapy for the object. Further, the driving gear 143a of the driving device 143 may be a one-stage gear, so backlash can be easily adjusted and operation accuracy can be improved.

Figure 9:
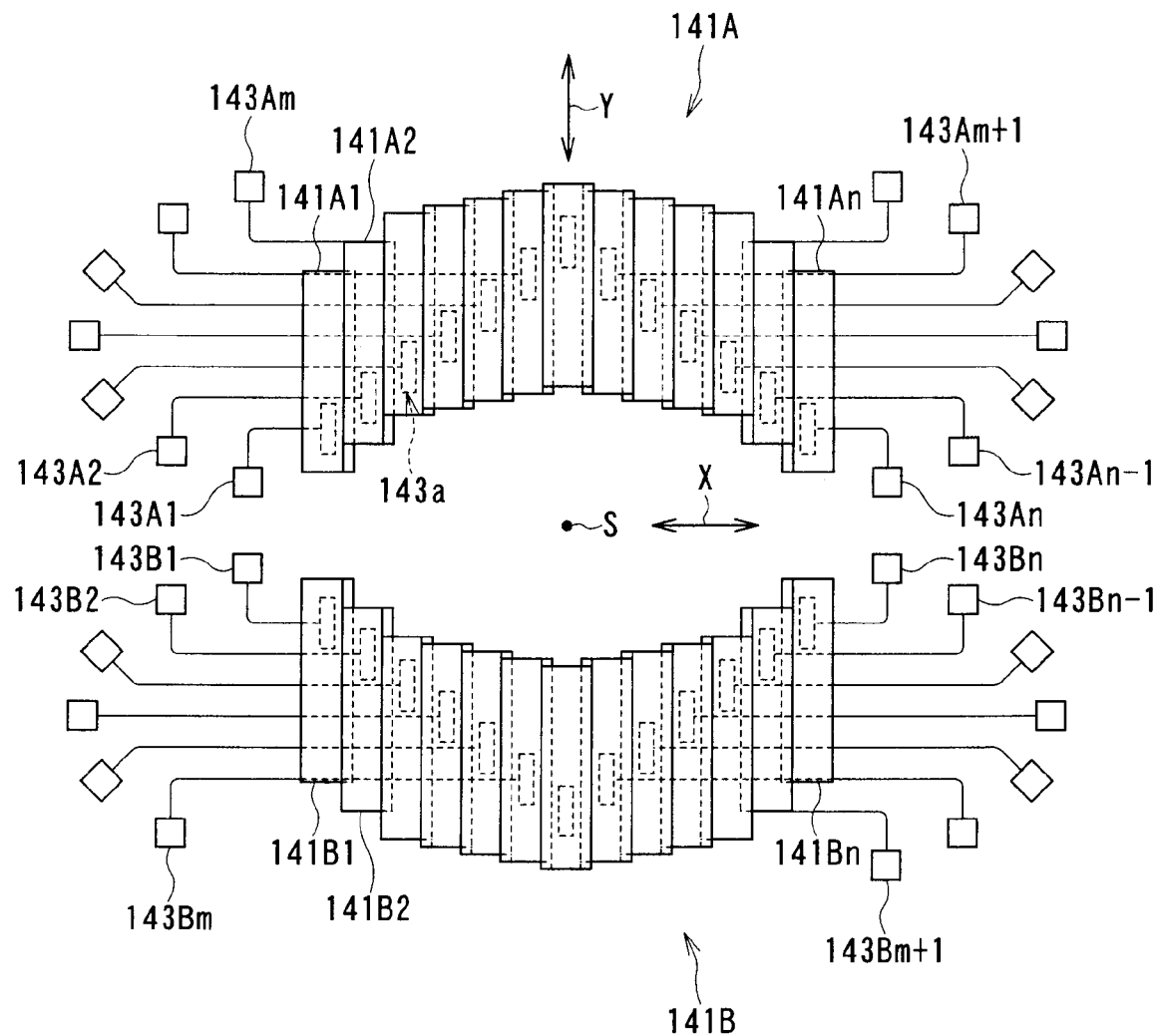
FIG. 9 is a top view of the leaves, which shows an arrangement example of the driving devices.
Figure 10:
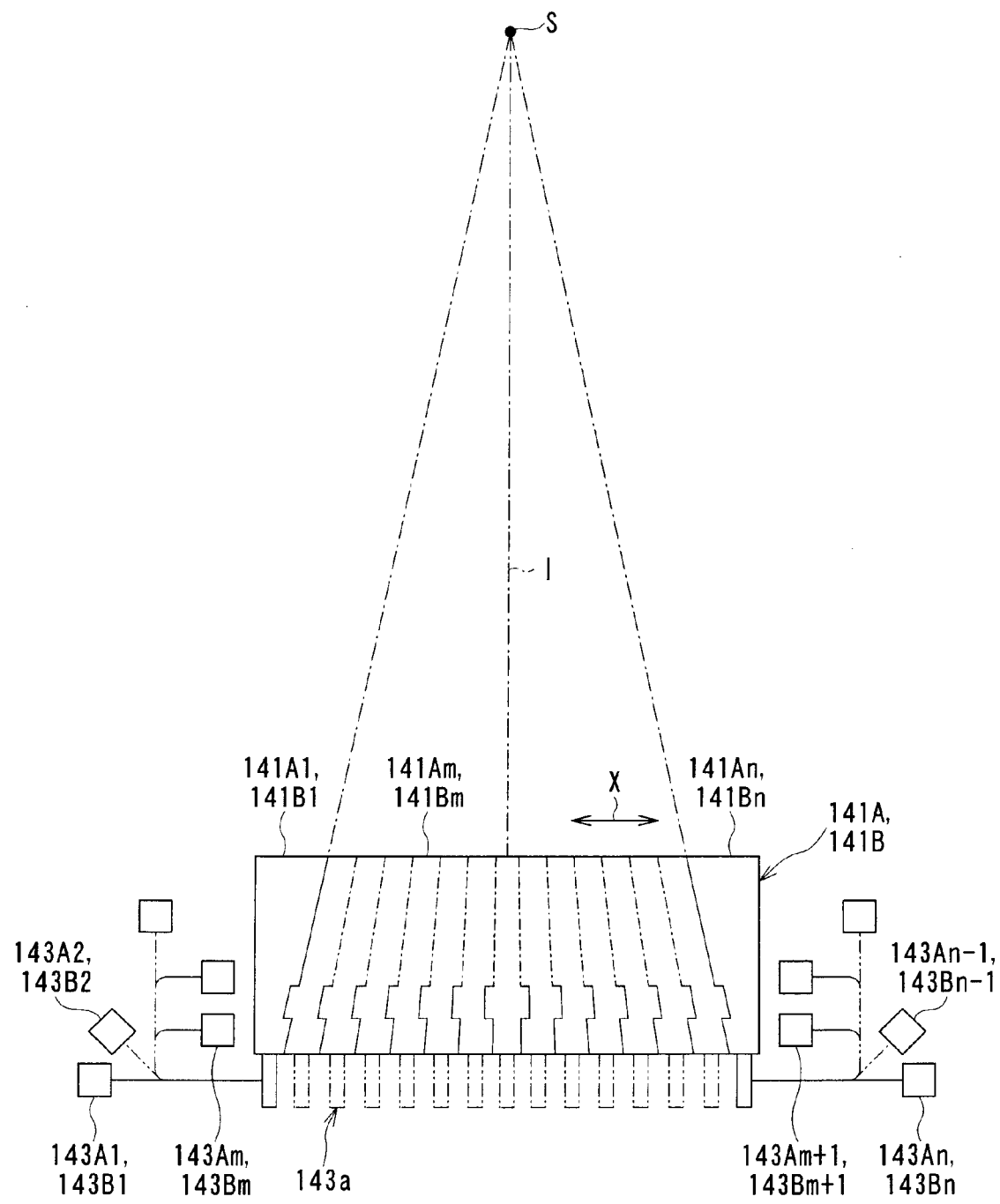
FIG. 10 is a side view of the leaves, which shows an arrangement example of the driving devices.

FIG. 9 is a top view of the leaves, which shows an arrangement example of the driving devices 143. FIG. 10 is a side view of the leaves, which shows an arrangement example of the driving devices 143.

In the radiation therapy apparatus of this embodiment, the driving devices 143 area arranged as shown in FIGS. 9 and 10, so the motor 143 achieves the very high degree of freedom of arrangement relative to the moving axis of each leaf 141 and thus can be placed even in a dead space of the container of the collimator 14.

Figure 15:
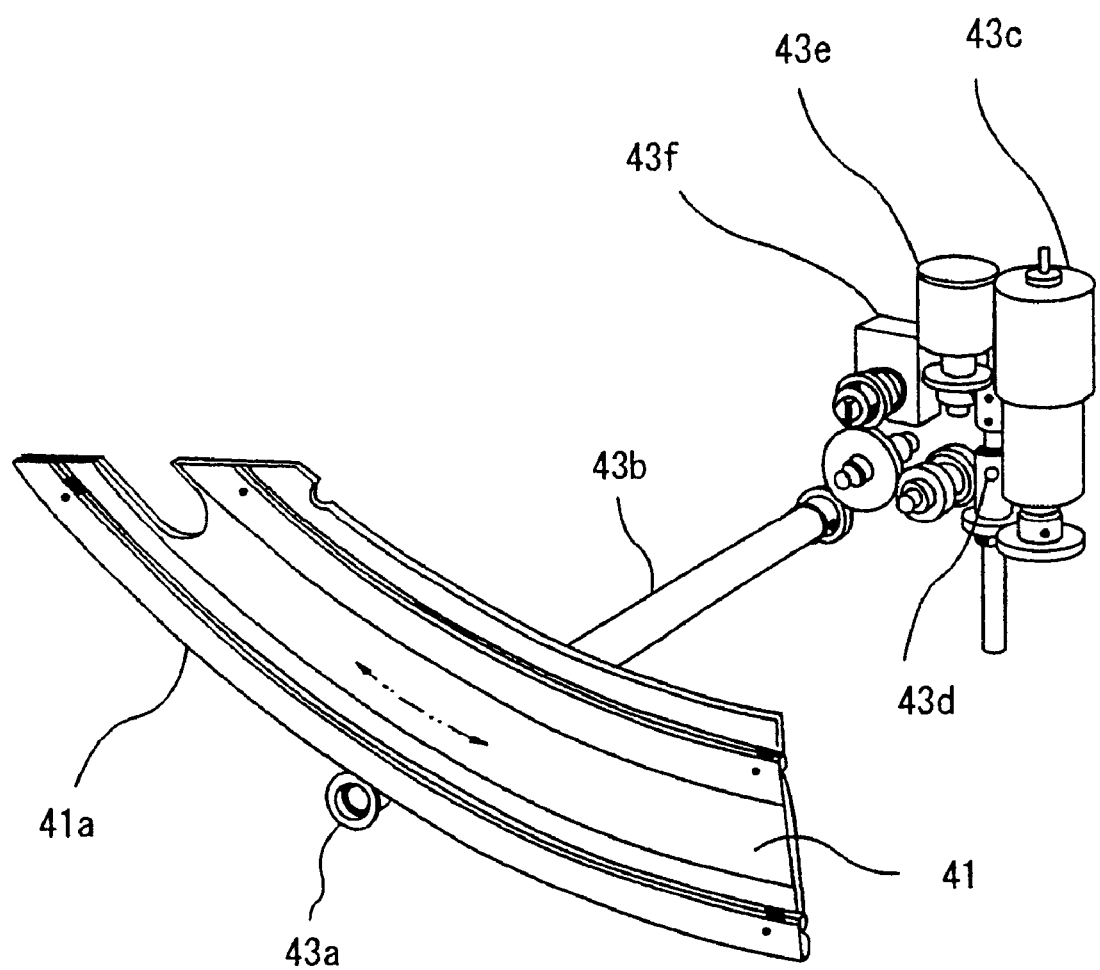
FIG. 15 schematically is one leaf of the second collimator and the driving device for driving the leaf.

If the torque motor 143c is equipped with an encoder, moving amounts of each leaf 141 can be easily detected, making it possible to simplify a complicated mechanism using a number of gears, and a potentiometer 43e or an encoder 43f in combination as shown in FIG. 15 to control the moving amounts. Further, a laser beam disclosed in "Japanese Patent Publication (Laid-open: KOKAI) No. 2004-275243" may be used to directly detect the moving amounts of each leaf 141 so as to set a position of each leaf 141.

Figure 11:
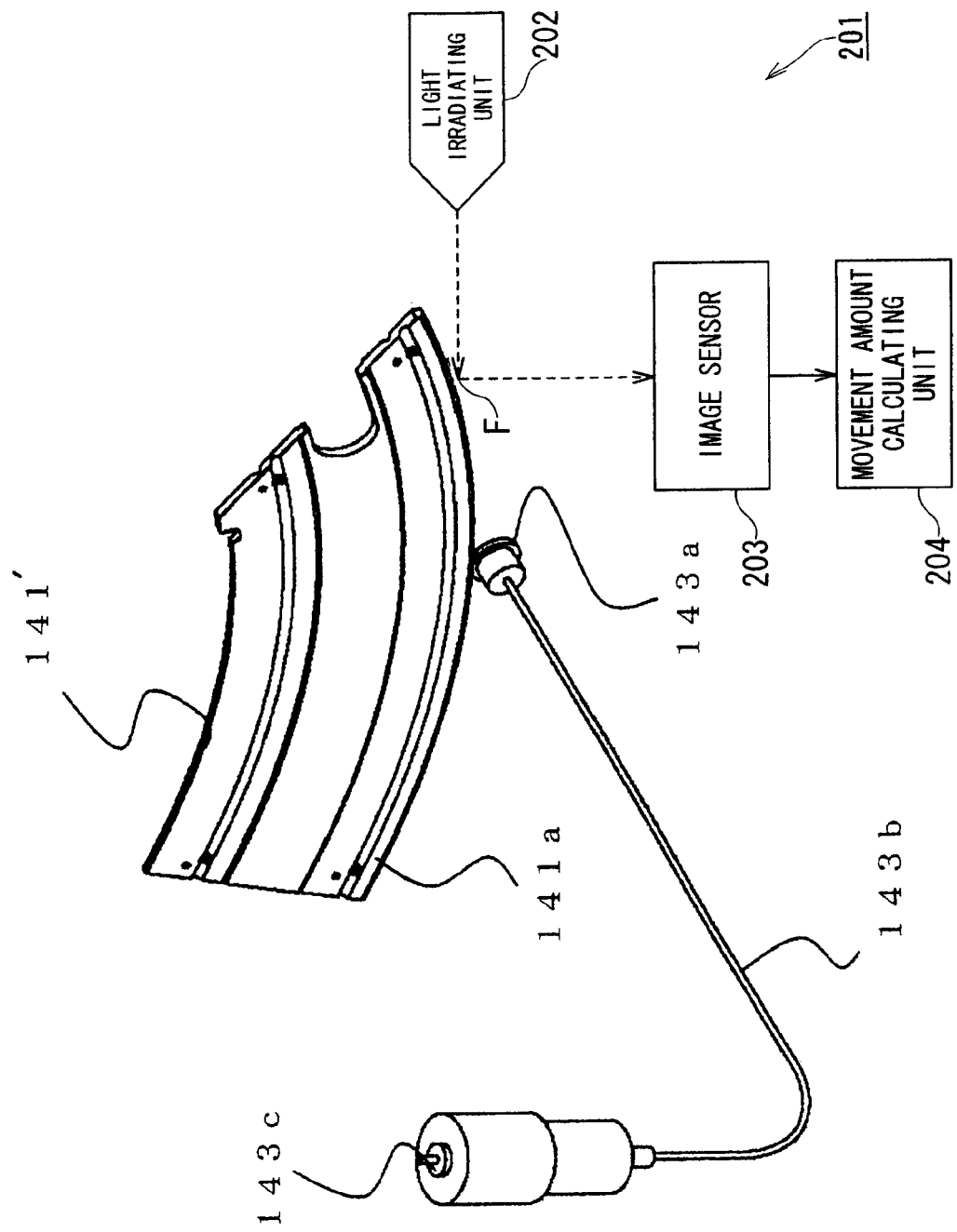
FIG. 11 schematically is the moving amount detecting unit with respect to the leaf.
Figure 12:
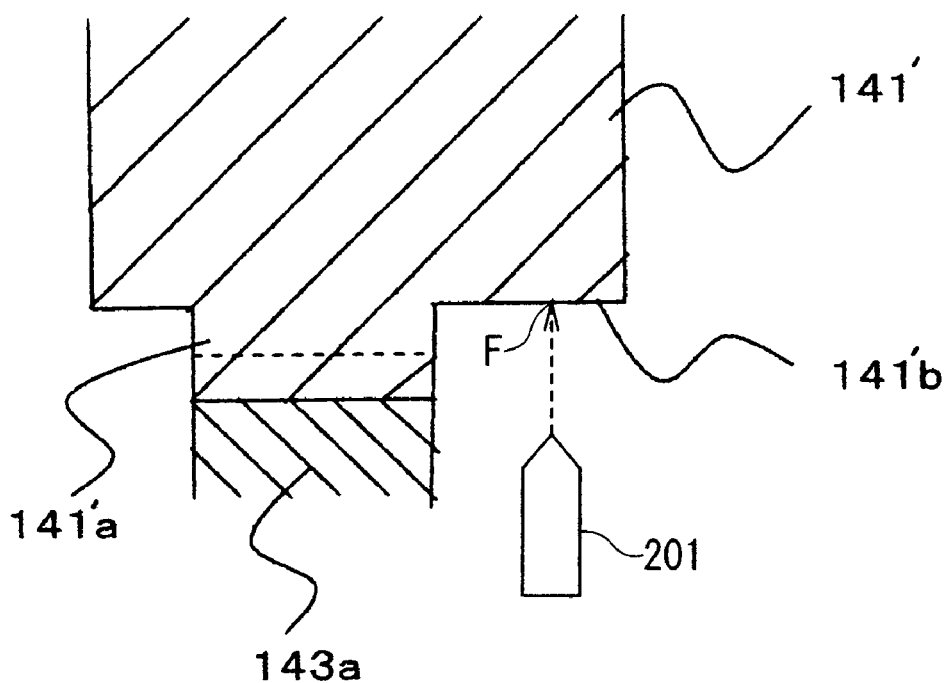
FIG. 12 is a sectional side view of the leaf, which elaborates on FIG. 11.
Figure 13:
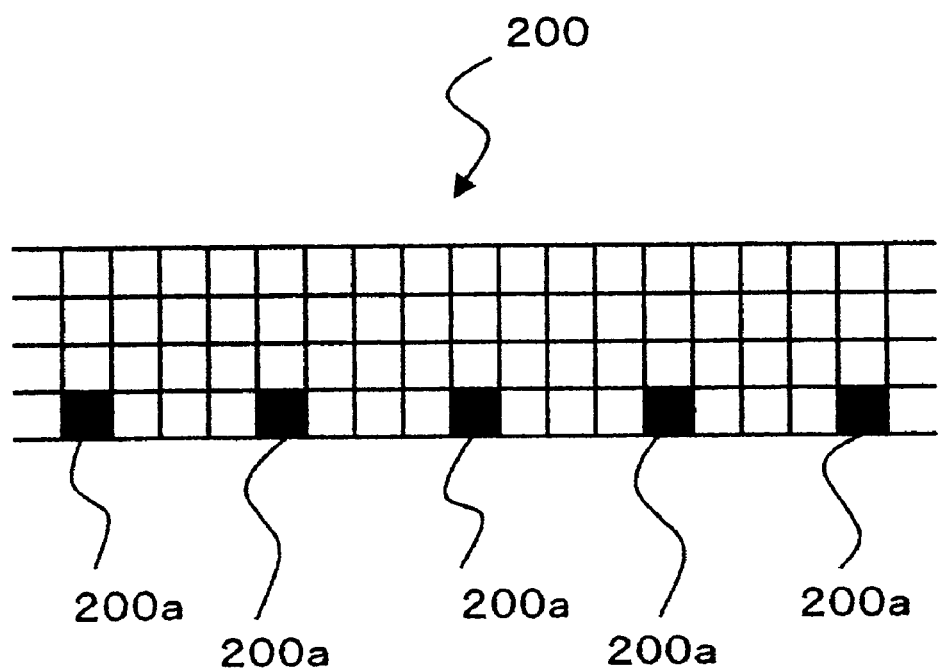
FIG. 13 is a pattern example formed on the leaf.

Moreover, the radiation therapy apparatus of this embodiment as shown in FIGS. 11 to 13 may include a leaf 141' attached to the above leaf 141 and having a predetermined pattern 200 along its outer circumference, and a moving amount detecting unit 201 for detecting plural positions of the leaf 141' based on the pattern 200 to detect the moving amounts of the leaf 141'. The detected moving amount of the leaf 141' is fed back to the control device 30. In this case, the moving amount detecting unit 201 includes a light irradiation unit 202, an imaging unit (image sensor) 203, and a moving amount calculating unit 204.

The light irradiating unit 202 secured in a predetermined position is composed of a light emitting diode etc. and applies light to a fixed point "F" on the moving path of the leaf 141 so as to illuminate a part of the pattern formed on the leaf 141'.

The image sensor 203 secured in a predetermined position is composed of a CCD (charge coupled device) camera etc. and obtains an image in an area including the fixed point "F" to obtain a fixed-point image.

The moving amount calculating unit 204 calculates the moving amount of the leaf 141' based on plural fixed-point images obtained with the image sensor 203.

The moving amount of the leaf 141' can be directly detected with the moving amount detecting unit 201 in a non-contact fashion, so a displacement or position detection error due to an influence of backlash or friction between gears can be suppressed. In the case of directly detecting the moving amount of each leaf using the above methods, any general motor, not a motor with a built-in encoder, can be used.

Referring to FIGS. 11 to 13, a method of directly detecting the moving amount of the leaf 141' in a non-contact fashion with the moving amount detecting unit 201 is described next. FIG. 11 schematically is the moving amount detecting unit 201 with respect to the leaf 141'. FIG. 12 is a sectional side view of the leaf 141', which elaborates on FIG. 11. FIG. 13 shows a pattern example formed on the leaf 141'.

As shown in FIG. 11, the light irradiating unit 202 illuminates the fixed point "F" on the moving path of the leaf 141, for example, on the moving path of the arc-shaped outer edge of the leaf 141' having a tooth 141'a cut therein. The image sensor 203 obtains the image in an area including the fixed point on the moving path of the arc-shaped to obtain a fixed-point image.

As shown in FIG. 12, the arc-shaped outer edge of the leaf 141' is divided along a moving direction of the leaf 141' into a portion for forming a tooth 141'a and a portion 141'b for forming the pattern 200 (see FIG. 13), not forming the tooth 141'a. In other words, the tooth 141'a and the pattern 200 are formed in line along a thickness direction of the leaf 141'. Then, the leaf 141' is engaged with the driving gear 143a, and the light irradiating unit 202 applies light onto the moving path of the portion 141'b of the arc-shaped outer edge, in which the pattern 200 is formed.

The pattern 200 is engraved along the arc-shaped outer edge of the leaf 141'. As shown in FIG. 13 by way of example, the pattern 200 is formed by engraving the outer edge at plural positions in a line at regular intervals. The pattern extends over a range similar to a movable range of the leaf 141'. The pattern includes unique patterns 200*a* in predetermined positions. The unique patterns 200*a* means characteristics patterns different from patterns of the other region of the pattern (inclusive of unpatterned region).

The pattern 200 includes consecutive blocks obtained by dividing, for example, an area measuring about 0.5 [mm]×0.5 [mm] into 16 blocks in a lattice form with the unique pattern 200*a* being formed at one corner of the lattice area. The unique patterns 200*a* are colored in black in FIG. 13 but may be uniformly ground more than the other blocks or have coarse grooves formed therein instead of being colored.

If the light irradiating unit 202 secured in a predetermined position applies light, the light illuminates a part of the pattern 200 as shown in FIG. 13. The irradiation direction of the light irradiating unit 202 is fixed. And the fixed point "F" is set in an absolute position not influenced and has a predetermined area. Further, the light irradiating unit 202 sets the fixed point "F" in the arc-shaped outer edge of the leaf 141' and sets an irradiation range including a part of the area including the pattern 200.

On the other hand, the image sensor 203 is set to image of an area including the fixed point "F" on the pattern 200 at regular intervals along the arc-shaped outer edge of leaf 141'. That is, the image sensor 203 receives light reflected by the fixed point "F" with time and obtains a fixed-point image at regular intervals. The fixed-point image includes a part of the pattern 200 engraved in the leaf 141'. The pattern 200 includes the unique pattern 200*a*, so the moving amount calculating unit 204 specifies a position of the unique pattern 200 obtained with the image sensor 203 to calculate a moving amount of the leaf 141' based on its time lag.

That is, the moving amount calculating unit 204 analyzes plural fixed-point images obtained on the time-series basis in accordance with the moving of the leaf 141' to thereby obtain a moving amount of the leaf 141'. If the leaf 141' moves, the pattern 200 engraved in the leaf 141' is moved together with the pattern 200. Thus, a position of the fixed point "F" is relatively changed on the pattern 200 including the unique pattern 200*a* in the plural fixed-point images obtained on the time-series basis. Hence, the detecting unit 201 can detect a moving amount of the leaf 141' by the moving amount calculating unit 204 specifying a position of the fixed point "F" relative to the pattern on the plural fixed-point images obtained on the time-series basis and determining displacement of the position.

The fixed-point image desirably includes a part or all of the unique pattern 200 regardless of the moving amount of the leaf 141'. Accordingly, the pattern 200 formed in the leaf 141' is desirably minimized in size. The reason the pattern 200 is divided into blocks each measuring about 0.5 mm per side with the pattern 200*a* set to one block is that the pattern 200*a* is set smaller than an area obtained with the image sensor 203.

Figure 14:
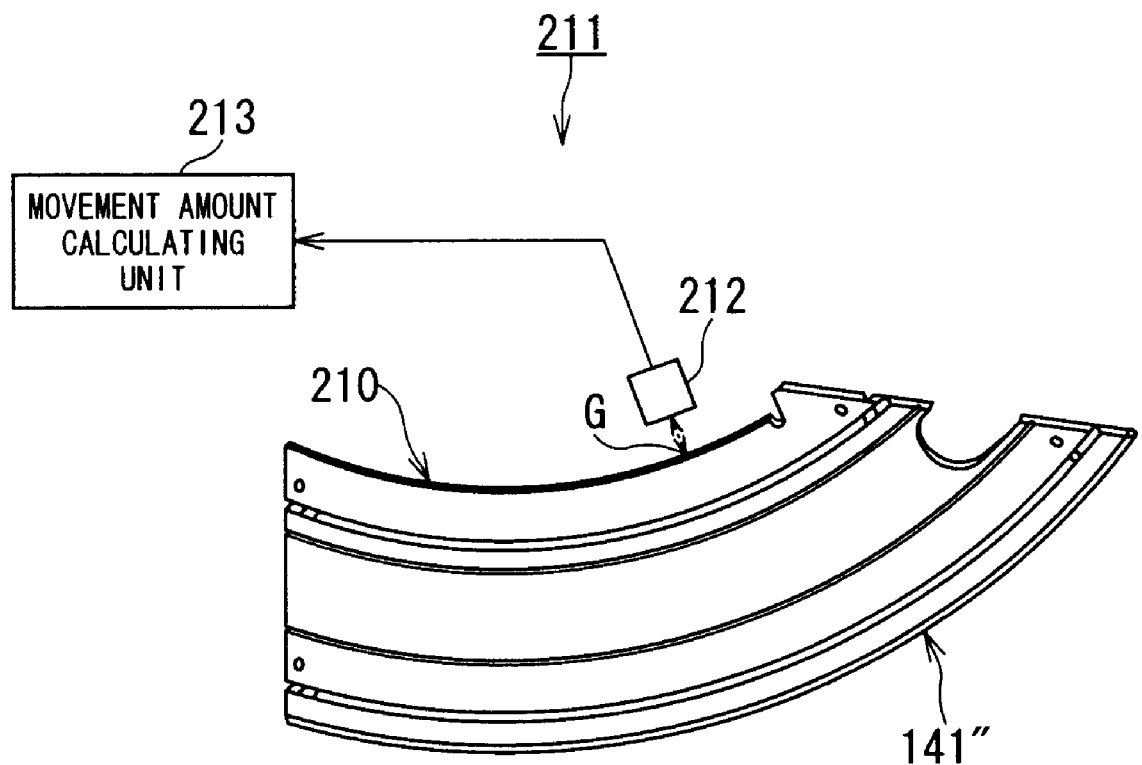
FIG. 14 schematically is the moving amount detecting unit with respect to the leaf.

As shown in FIG. 14, the radiation therapy apparatus of this embodiment may include a leaf 141", which is provided to the leaf 141 and to which a magnetic tape 210 storing magnetic information is attached (affixed) at regular intervals along its (inner or outer) circumference, and a moving amount detecting unit 211 for detecting plural positions of the leaf 141" based on the magnetic information to determine a moving amount of the leaf 141". The detected moving amount of the leaf 141" is fed back to the control device 30. In this case, the moving amount detecting unit 211 includes a magnetic detection unit (magnetic sensor) 212 and a moving amount calculating unit 213.

The magnetic sensor 212 detects magnetic information at a fixed point "G" on the moving path of the leaf 141" so as to obtain magnetic information from the magnetic tape 210 attached to the leaf 141". Here, the magnetic tape 210 has a predetermined distance (several micrometers) from the magnetic detecting unit 212. Thus, there is no influence of change over time such as abrasion. If magnetic information is recorded onto the magnetic tape 210 at regular intervals along the circumference of the leaf 141", a recording pitch corresponds to detection accuracy. Further, the tape can be magnetized on the order of micrometer, so the position of the leaf 141" can be detected.

The moving amount calculating unit 213 calculates a moving amount of the leaf 141" based on magnetic information detected with the magnetic sensor 212. The magnetic information is output as a pulse signal and thus is subjected to digital processing similar to signal processing of a conventional encoder, so its accuracy and reliability are high.

According to the radiation therapy apparatus of this embodiment, a torque wire having a high rotation following capability is used to allow transmission of a torque of the motor as a driving source to a tip end with accuracy while keeping a high flexibility to a bent portion. Accordingly, the torque wire can transmit a torque of the motor to a driving gear with accuracy regardless of orientation and angle of the motor, making it possible to move the leaves concentrically along the arc-shaped path about the radiation source to get close to/away from each other.

Therefore, the motor can achieve the very high degree of freedom of arrangement relative to the moving axis of the leaves and can be placed in a dead space in the collimator. In short, an internal space of the collimator device 14 can be efficiently utilized, and the number of leaves can be increased without enlarging the collimator device 14. As a result, the irradiation field "U" can be matched more with a treatment site without reducing the space for the treatment. This enables safer radiotherapy for the object. Further, the driving gear 143*a* of the driving device 143 may be a one-stage gear, so backlash can be easily adjusted and operation accuracy can be improved.

Further, according to the radiation therapy apparatus of this embodiment, the moving amount of each leaf can be easily detected using a torque motor with a built-in encoder, making it possible to simplify a complicated mechanism using a number of gears, and a potentiometer or an encoder in combination to control the moving amount.

Further, according to the radiation therapy apparatus of this embodiment, a displacement or position detection error due to an influence of backlash or friction between gears can be suppressed. Hence, a leaf position can be accurately detected and the irradiation field "U" can be accurately matched with an affected area.

What is claimed is:

1. A radiation therapy apparatus comprising:
   a multi-leaf collimator device having a pair of collimator components which respectively include a plurality of leaves arranged close to one another such that the leaves face one another across an irradiation axis, and configured to set a desired irradiation field by individually moving the leaves;
   a driving gear engaged with a gear tooth of the each leaf, respectively;
   a torque wire connected to a shaft center of the driving gear, respectively;
   a driving unit configured to drive the driving gears through the torque wire;
   a plurality of patterned leaves obtained by forming a predetermined pattern in the leaves in a moving direction along its moving path; and a moving amount detecting unit configured to detect a moving amount of the each patterned leaf respectively, by obtaining a plurality of positions of the each patterned leaf based on the pattern.

2. The radiation therapy apparatus according to claim 1, wherein the driving unit comprises a torque motor with a built-in encoder.

3. The radiation therapy apparatus according to claim 1, wherein the moving amount detecting unit includes:
- a light irradiating unit configured to apply light to a fixed point on the moving path of the patterned leaves so as to illuminate a part of the pattern;
- an imaging unit configured to obtain an image in an area including the fixed point on the pattern to obtain a fixed-point image; and
- a moving amount calculating unit configured to calculate the moving amount of the each patterned leaf based on the fixed-point image obtained with the imaging unit.

4. The radiation therapy apparatus according to claim 1, wherein the pattern is formed on an outer side of the each leaf, respectively.

5. A radiation therapy apparatus comprising:
- a multi-leaf collimator device having a pair of collimator components which respectively include a plurality of leaves arranged close to one another such that the leaves face one another across an irradiation axis, and configured to set a desired irradiation field by individually moving the leaves;
- a driving gear engaged with a gear tooth of the each leaf, respectively;
- a torque wire connected to a shaft center of the driving gear, respectively;
- a driving unit configured to drive the driving gears through the torque wire;
- a plurality of magnetic tape-attached leaves obtained by attaching a magnetic tape storing magnetic information to the leaves at regular intervals along the moving direction on its moving path; and
- a moving amount detecting unit configured to detect a moving amount of the each magnetic tape-attached leaf respectively, by obtaining a plurality of positions of the each magnetic tape-attached leaf based on the magnetic information.

6. The radiation therapy apparatus according to claim 1, wherein the leaves have an arc-shaped moving path.

7. The radiation therapy apparatus according to claim 1, wherein the leaves have a linear moving path.

8. The radiation therapy apparatus according to claim 5, wherein the driving unit comprises a torque motor with a built-in encoder.

9. The radiation therapy apparatus according to claim 5, wherein the leaves have an arc-shaped moving path.

10. The radiation therapy apparatus according to claim 5, wherein the leaves have a linear moving path.

* * * * *